United States Patent [19]

Johnson, Jr.

[11] Patent Number: 4,690,783

[45] Date of Patent: Sep. 1, 1987

[54] METHOD OF PREPARING ROSIN ESTER FROM POLYOL WITH PHOSPHOROUS ACID CATALYST

[75] Inventor: Robert W. Johnson, Jr., Savannah, Ga.

[73] Assignee: Union Camp Corporation, Wayne, N.J.

[21] Appl. No.: 902,464

[22] Filed: Aug. 29, 1986

[51] Int. Cl.$^4$ ................................................ C08F 1/04
[52] U.S. Cl. ..................................... 260/104; 260/97; 260/97.5
[58] Field of Search ................... 260/104, 97, 97.5

[56] References Cited

U.S. PATENT DOCUMENTS

| | | | |
|---|---|---|---|
| 2,729,660 | 1/1958 | Harrison | 260/410.6 |
| 4,172,070 | 10/1979 | Scharrer et al. | 260/104 |
| 4,548,746 | 10/1985 | Duncan et al. | 260/104 |

*Primary Examiner*—Harold D. Anderson
*Attorney, Agent, or Firm*—Kane, Dalsimer, Kane, Sullivan and Kurucz

[57] ABSTRACT

Phosphorous acid is used to catalyze the esterification of rosin with a polyol. The method is an improvement in that reaction time is shortened and the ester product exhibits improved color and oxygen stability.

12 Claims, No Drawings

METHOD OF PREPARING ROSIN ESTER FROM POLYOL WITH PHOSPHOROUS ACID CATALYST

This invention relates to a method for preparing rosin esters and more particularly is concerned with the manufacture of polyol esters of tall oil rosin.

BACKGROUND OF THE INVENTION

Rosin is a well known, commercially available product which is comprised of mainly $C_{20}$ fused-ring monocarboxylic acids with abietic type acids being typical components of rosin. Rosin is capable of being subjected to various types of chemical conversions, of which esterification is one of the more commonly performed. The rosin esters which are obtained as a result of esterification are useful in a wide variety of different applications; for example, as tackifiers in hot-melt adhesive compositions and the like. In most applications where rosin esters are employed, it is highly desirable that the rosin ester be as light in color as possible, have a relatively high softening point, and be resistant against oxidation.

Various methods have heretofore been suggested for the esterification of rosin. All the methods which have heretofore been suggested have, however, had one or more substantial disadvantages. Certain of the suggested methods required relatively long reaction times. Other methods caused a substantial increase in the color of the final product as compared to the starting rosin. Still other of the suggested methods required relatively expensive catalyst and often there was a evolution of obnoxious fumes, highly toxic gases, or flammable gases during the esterification reaction.

The method which was traditionally used for the esterification of rosin involved the use of a strong basic catalyst such as calcium oxide to promote the esterification reaction. This method was found to be unsatisfactory in that it required extremely long reaction times and the resulting esterified product was typically highly colored as compared to the starting rosin.

It was also suggested to use aliphatic or aromatic esters of phosphorous acid as the catalyst in the esterification process. The time of reaction using this class of catalyst was substantially decreased as compared to the method employing basic catalysts, and the final product tended to be substantially lighter in color. However, the suggested catalysts were relatively expensive to purchase and during the reaction decomposed causing an evolution of highly obnoxious odors.

It was also suggested to use phosphinic acid as the catalyst for the esterification. Reasonable reaction times were obtained using phosphinic acid as the catalyst, and the resulting product did have a relatively light color. The use of phosphinic acid as the catalyst, however, was found to have a number of inherent and distinct disadvantages. Initially, the cost of the catalyst was relatively high. Since the phosphinic acid catalyst is not recovered from the reaction product and, in fact, appears to decompose during the esterification reaction, the overall manufacturing cost of the rosin esters was increased. An additional problem which was found when using phosphinic acid as the catalyst was that during the esterification process the catalyst apparently decomposed and as a result, phosphine, a deadly toxic gas was released along with other inflammable gases and created considerable manufacturing problems.

What would be highly desirable would be a method for manufacturing rosin esters which could be conducted in a relatively short reaction time, would result in rosin esters having a relatively light color, which would use relatively inexpensive catalysts, and which during the reaction process would not result in the evolution of large quantities of obnoxious, toxic, or flammable gases.

SUMMARY OF THE INVENTION

A method is disclosed for the preparation of rosin esters in which rosin is esterified with a polyol in the presence of a catalytically effective amount of phosphorous acid.

DETAILED DESCRIPTION OF THE INVENTION

The rosins which may be esterified by the method of the invention are well known compounds as are methods of their preparation. Rosin is mainly a mixture of $C_{20}$ fused-ring, monocarboxylic acids, typified by abietic acids. The type of rosin which can be employed in the method of this invention includes gum rosin, wood rosin, and tall oil rosin. The method of the invention is particularly advantageous when applied to esterification of tall oil rosin. The rosin may be hydrogenated, disproportionated, or polymerized rosin as well as crude, untreated rosin.

The polyols which can be employed in the method of the invention are also well known and are represented by diols such as ethylene glycol, propylene glycol, diethylene glycol, triethylene glycol, tetraethylene glycol, trimethylene glycol, triols such as glycerol, tetrols such as pentaerythritol, hexols such as mannitol and sorbitol, and like polyols. The method of the invention is particularly advantageous when the polyol selected is pentaerythritol.

The esterification method of the invention is carried out in the presence of a catalytic effective amount of phosphorous acid. The relative amount which is employed can be varied over a wide range, but, typically, is generally within the range of from about 0.02 to 1.0 percent and preferably 0.1 to 0.5 percent based on the weight of the rosin.

The esterification is advantageously carried out by combining the rosin with at least an equivalent stoichiometric amount of the polyol and preferably up to about 20 percent excess of the polyol in a suitable reaction vessel. A catalytically effective amount of phosphorous acid is added to the reaction mixture. The phosphorous acid catalyst can be added to the reaction mixture as a separate component at the time the reaction mixture is prepared. It is also possible and often advantageous to initially pretreat the rosin reactant by initially bringing it into intimate contact with the phosphorous acid in a pretreatment step. Thereafter, the pretreated rosin can be blended with the polyol reactant to provide the reaction mixture. The reaction mixture is then heated to a temperature within the range of from about 150° C. to 300° C. and preferably 180° C. to 280° C.

Progress of the esterification may be followed by conventional analyses of the reaction mixture to determine the acid number. The esterification may be terminated to any desired acid number. In general, the reaction is accepted as sufficiently complete when the acid number drops to 15 or lower.

After the esterification has been completed to the desired acid number, the resulting rosin ester can be neutralized if desired by adding a suitable amount of a base, such as sodium hydroxide, to the reaction mixture in the reaction vessel and stirring until the neutralization is completed.

The following examples describe the manner and the process of making and using the invention and set forth the best mode of carrying out the invention, but are not to be considered as limiting the invention.

The softening points were determined by the Ball and Ring Method of ASTM test method 28-58T.

EXAMPLE 1

This is not an example of the invention, but is made for purposes of comparison.

To a suitable reaction vessel equipped with a stirrer and thermometer were added 100 parts of disproportionated tall oil rosin having a color of 4 Gardner. There are then added 11 parts of pentaerythritol and 0.05 percent calcium oxide as the catalyst, based on the weight of the rosin. The mixture was heated to 275° C. for about eight hours. The resultant rosin pentaerythritol ester had a color of 8 Gardner, an acid number of 9.3, and a softening point of 99° C.

EXAMPLE 2

This is not an example of the invention, but is made for purposes of comparison.

To a suitable reaction vessel equipped with a stirrer and thermometer were added 100 parts of disproportionated tall oil rosin having a color of 4 Gardner. There are then added 11 parts of pentaerythritol and 0.2 percent of phosphinic acid as the catalyst, based on the weight of the rosin. The mixture was then heated to 275° C. for about eight hours. During the course of the reaction, the evolution of gaseous product was monitored, and the gaseous mixture was analyzed with regard to its content. It was found that the gases which were evolved during the reaction included substantial amounts of phosphine as well as hydrogen. The resulting rosin pentaerythritol ester was found to have a color of 4+ Gardner, an acid number of 4.8, and a softening point of 100.5° C.

EXAMPLE 3

The procedure of Example 2 was repeated except 0.2 percent phosphorous acid was used as catalyst instead of 0.2 percent of phosphinic acid added over a period of 2 hours while heating the mixture to 275° C. and continuing the reaction for a total of 5.5 hours. There are no indications of the evolution of phosphine or other toxic gases. The resulting ester had a color of 4+ Gardner, and acid number of 4.8, and a softening point of 100.5° C.

EXAMPLE 4

The procedure of Example 3 was repeated except the starting disproportionated rosin had a color of 2+ Gardner and heating was for 6 hours. The resulting ester had a color of 2+ Gardner, and acid number of 6.7, and softening point of 105° C.

EXAMPLE 5

To a suitable reaction vessel equipped with a stirrer and thermometer were added 100 parts of disproportionated tall oil rosin having a color of 4 Gardner. There is then added 0.2 percent phosphorous acid and the mixture heated to 200° C. and held for 1 hour. Pentaerythritol, 11 parts, is then added and the mixture heated to 275° for 6 hours. The resultant rosin pentaerythritol ester had a color of 4+ Gardner, an acid number of 8.7, and a softening point of 99° C.

EXAMPLE 6

Aliquots of the resins obtained in Examples 3 and 4, supra were neutralized to the extent of 40 percent of the phosphorous acid, with sodium hydroxide. The neutralized aliquots were then tested by heating to 177° C. in a hot-melt adhesive formulation in the open atmosphere and observing the percentage of skinning which occurred over periods of time and the degree of viscosity change. The test results are given in Table 1 below and compared with samples not neutralized. The reduction in viscosity in the neutralized samples was measured.

TABLE 1

| Example | Color, G Initial | Color, G Final | Hot-Melt Properties Skimming, % (hr) 24 | 48 | 96 | Visc. Change % |
|---|---|---|---|---|---|---|
| 3 not neutralized | 3+ | 9− | 0 | 2 | 2 | +50 |
| 3 neutralized | 4 | 9− | 0 | 10 | 10 | −7 |
| 4 not neutralized | 3+ | 8− | 0 | 5 | 5 | +35 |
| 4 neutralized | 4+ | 8 | 0 | 0 | 0 | +14 |

What is claimed is:

1. A method of preparing a polyol ester of rosin, which comprises esterifying a rosin with a polyol in the presence of a catalytically effective amount of phosphorous acid.

2. The method of claim 1 wherein the amount of phosphorous acid is within the range of from about 0.02 to 1.0 percent by weight of the rosin.

3. The method of claim 1 wherein the amount of phosphorous acid is within the range of from about 0.1 to 0.5 percent by weight of the rosin.

4. The method of claim 1 wherein the rosin is tall oil rosin.

5. The method of claim 1 wherein the rosin is a disproportionated rosin.

6. The method of claim 1 wherein the polyol is pentaerythritol.

7. The method of claim 1 wherein the rosin is tall oil rosin and the polyol is pentaerythritol.

8. The method of claim 1 wherein the esterifying is carried out at a temperature within the range of from about 150° C. to 300° C.

9. The method of claim 1 wherein the esterifying is carried out at a temperature within the range of from about 180° C. to 280° C.

10. The method of claim 1 wherein the esterifying is carried out under an inert gas atmosphere.

11. The method of claim 1 wherein the rosin is initially pretreated with the phosphorous acid.

12. The method of claim 1 wherein, after esterifying, the resultant polyol ester of rosin is neutralized at least partially.

* * * * *